(12) United States Patent
Chen et al.

(10) Patent No.: US 12,426,919 B1
(45) Date of Patent: Sep. 30, 2025

(54) INTERVENTIONAL NEEDLE FIXING DEVICE FOR TUMOR CLINICAL TREATMENT

(71) Applicant: GUANGZHOU INSTITUTE OF CANCER RESEARCH, THE AFFILIATED CANCER HOSPITAL, GUANGZHOU MEDICAL UNIVERSITY, Guangdong (CN)

(72) Inventors: Guoshuo Chen, Guangdong (CN); Zhimei Wen, Guangdong (CN); Jiajun Li, Guangdong (CN)

(73) Assignee: GUANGZHOU INSTITUTE OF CANCER RESEARCH, THE AFFILIATED CANCER HOSPITAL, GUANGZHOU MEDICAL UNIVERSITY, Guangzhou (CN)

( * ) Notice: Subject to any disclaimer, the term of this patent is extended or adjusted under 35 U.S.C. 154(b) by 0 days.

(21) Appl. No.: 19/211,125

(22) Filed: May 16, 2025

Related U.S. Application Data

(63) Continuation of application No. PCT/CN2025/087417, filed on Apr. 7, 2025.

(51) Int. Cl.
| | |
|---|---|
| *A61B 17/34* | (2006.01) |
| *A61B 90/00* | (2016.01) |
| *A61B 90/11* | (2016.01) |
| *A61B 17/00* | (2006.01) |

(52) U.S. Cl.
CPC .......... *A61B 17/3403* (2013.01); *A61B 90/03* (2016.02); *A61B 90/11* (2016.02); *A61B 2017/00398* (2013.01); *A61B 2017/00477* (2013.01); *A61B 2017/00991* (2013.01); *A61B 2017/3409* (2013.01); *A61B 2090/034* (2016.02)

(58) Field of Classification Search
CPC ...... A61B 17/3403; A61B 2017/00398; A61B 2017/00477; A61B 2017/00991; A61B 2017/3409; A61B 90/11; A61B 90/03; A61B 2090/034
USPC ......................................................... 606/13
See application file for complete search history.

(56) References Cited

U.S. PATENT DOCUMENTS

| | | | | |
|---|---|---|---|---|
| 10,646,295 | B2* | 5/2020 | Stoianovici | A61B 90/11 |
| 2016/0256233 | A1* | 9/2016 | Pandey | A61B 5/055 |
| 2017/0151416 | A1* | 6/2017 | Kutikov | A61B 17/3478 |
| 2017/0252115 | A1* | 9/2017 | Stoianovici | A61B 90/11 |

(Continued)

*Primary Examiner* — Ahmed M Farah

(57) ABSTRACT

The present disclosure provides an interventional needle fixing device for tumor clinical treatment, including an interventional needle adjustment mechanism. The interventional needle adjustment mechanism includes a roll adjustment assembly, a pitch adjustment assembly, a rotating assembly and a needle tube assembly. In the present disclosure, by arranging the interventional needle adjustment mechanism, when facing tumor lesions in different positions, doctors make the needle tube assembly realize left or right roll adjustment in a horizontal direction through the roll adjustment assembly, thereby accurately aligning a target area. At the same time, the pitch adjustment assembly can control the needle tube assembly to pitch upward or downward in a vertical direction, thereby meeting the diversified requirements of interventional needle angles in various complex surgical scenes, and improving the flexibility and accuracy of interventional needle puncture.

10 Claims, 8 Drawing Sheets

(56) References Cited

U.S. PATENT DOCUMENTS

| | | | |
|---|---|---|---|
| 2020/0054378 A1* | 2/2020 | Kincaid | A61B 6/12 |
| 2021/0000499 A1* | 1/2021 | Fenster | A61B 6/5205 |
| 2023/0134815 A1* | 5/2023 | Nevo | A61B 5/061 |
| | | | 600/424 |

* cited by examiner

INTERVENTIONAL NEEDLE FIXING DEVICE FOR TUMOR CLINICAL TREATMENT

CROSS-REFERENCE TO RELATED APPLICATIONS

This application is a continuation of PCT/CN2025/087417, filed on Apr. 7, 2025, the entire contents of which are incorporated herein by reference.

TECHNICAL FIELD

The present disclosure relates to the technical field of tumor clinical treatment instruments, and in particular to an interventional needle fixing device for tumor clinical treatment.

BACKGROUND

Interventional needle is a medical instrument used to puncture into specific parts of the human body in tumor interventional therapy to achieve objectives of diagnosis or treatment, and establish a channel for subsequent operations including drug injection, tissue sampling and ablation. In the tumor clinical treatment, the use of interventional needles is usually assisted by fixing devices to improve the accuracy and safety of operation.

At present, the interventional needle fixing device used in the tumor clinical treatment often requires medical staff to manually adjust the position many times in the actual operation process, which consumes time and energy. When doctors are ready to insert the interventional needle into the patient's tissue, the inclination angle of the insertion needle needs to be adjusted and the appropriate puncture position needs to be selected before the insertion needle can be inserted. However, if the interventional needle is over-fixed, it will be greatly inconvenient to adjust the flexible adjustment of the needle angle. Even if the interventional needle is successfully inserted into the patient, the inclined position of the needle often needs to be slightly adjusted.

Many existing interventional needle fixing devices have limitations in inclined angle adjustment, which cannot meet the diversified angle requirements in complex surgical scenarios. When interventional treatment is performed for some tumors with special positions, interventional needles are required to puncture at a large angle or a special angle, while traditional fixing devices are difficult to achieve such a wide angle adjustment, which limits the implementation of surgical plans. Secondly, some interventional needle fixing devices are generally inconvenient to adjust the position thereof after mounting and fixing, which makes it inconvenient to flexibly adjust the positions thereof according to the patient's puncture needs.

SUMMARY

The present disclosure provides an interventional needle fixing device for tumor clinical treatment to solve the problem that an angular position of the interventional needle fixing device in the related art is inconvenient to adjust.

The present disclosure provides an interventional needle fixing device for tumor clinical treatment, including a supporting seat, a displacement regulation mechanism, an upright column, a lifting mechanism and an interventional needle adjustment mechanism.

The displacement regulation mechanism includes a driving assembly, a moving assembly and two limiting rods. The driving assembly is mounted in the supporting seat, and the moving assembly is mounted on the driving assembly. The two limiting rods are fixedly arranged at the supporting seat, and the limiting rods are slidably connected to the moving assembly. The upright column is fixedly mounted on one side of the moving assembly. The lifting mechanism is arranged inside the upright column. The interventional needle adjustment mechanism includes a roll adjustment assembly, a pitch adjustment assembly, a rotating assembly and a needle tube assembly. The roll adjustment assembly is fixedly mounted in the lifting mechanism. The pitch adjustment assembly is mounted on the roll adjustment assembly. The rotating assembly is slidably connected to the roll adjustment assembly, and the needle tube assembly is mounted on the rotating assembly.

According to the interventional needle fixing device for tumor clinical treatment provided by the present disclosure, the roll adjustment assembly includes a first motor, a supporting frame, a positioning rod and an annular frame. The first motor is fixedly mounted in the lifting mechanism, and the supporting frame is fixedly connected to an output end of the first motor. The positioning rod is movably embedded at the supporting frame. The annular frame is fixedly connected to the positioning rod.

According to the interventional needle fixing device for tumor clinical treatment provided by the present disclosure, the pitch adjustment assembly includes a second motor, a first gear and a second gear. The second motor is fixedly mounted on a surface of the supporting frame. The first gear is fixedly connected to an output end of the second motor. The second gear is fixedly mounted on the positioning rod, and the first gear is meshed with the second gear.

According to the interventional needle fixing device for tumor clinical treatment provided by the present disclosure, the rotating assembly includes a third motor, a third gear, a positioning frame plate, two sliding plates and a gear ring. The third motor is fixedly mounted on the positioning frame plate. One end of the third gear is fixedly connected to an output end of the third motor, and the other end is rotatably connected to the positioning frame plate. The two sliding plates are fixedly connected to two ends of the positioning frame plate. The two side surfaces of the annular frame are disposed with sliding grooves movably connected to the two sliding plates. The gear ring is fixedly sleeved on an outer surface of the annular frame, and the third gear is meshed with the gear ring.

According to the interventional needle fixing device for tumor clinical treatment provided by the present disclosure, the needle tube assembly includes a mounting frame, a syringe and a needle guide tube. The mounting frame is fixedly connected to the positioning frame plate. The syringe is fixedly mounted on a surface of the mounting frame. The needle guide tube is embedded and mounted in the syringe.

According to the interventional needle fixing device for tumor clinical treatment provided by the present disclosure, the driving assembly includes two driving motors, two lead screws, two fixing plates and a gear I. The two driving motors are fixedly arranged on two sides of an inner cavity of the supporting seat. Ends of the two lead screws are fixedly connected to output ends of the two driving motors, and the other ends are rotatably connected to the two fixing plates. The two fixing plates are fixedly mounted in the supporting seat. The gear I is meshed with the two lead screws.

According to the interventional needle fixing device for tumor clinical treatment provided by the present disclosure, the moving assembly includes a gear II, a moving seat, a gear rack and a sliding rod. The gear II is fixedly connected to the gear I. The moving seat is movably connected to the two limiting rods. The gear rack is slidably connected to the moving seat, and the gear rack is meshed with the gear II. The sliding rod is fixedly connected to the gear rack and is movably embedded on a surface of the moving seat.

According to the interventional needle fixing device for tumor clinical treatment provided by the present disclosure, a positioning mechanism is further included, which is fixedly mounted on a lower surface of the supporting seat. The positioning mechanism includes a clamping base, two screw rods, two connecting rods, an electric push rod and a clamping plate. The clamping base is fixedly mounted on the supporting seat. Ends of the two screw rods are movably connected to a lower surface of the clamping base, and the two screw rods are fixedly connected to the two connecting rods. The electric push rod is movably connected to the two connecting rods. The clamping plate is screwed with the two screw rods. A lower surface of the clamping plate and an upper surface of the clamping base are arranged with anti-slip pads.

According to the interventional needle fixing device for tumor clinical treatment provided by the present disclosure, the lifting mechanism includes an electric telescopic rod, a lifting block and a mounting housing. The electric telescopic rod is fixedly mounted at a bottom of an inner cavity of the upright column. The lifting block is fixedly mounted at a top of the electric telescopic rod. The mounting housing is fixedly connected to the lifting block, and the first motor is fixedly mounted inside the mounting housing.

According to the interventional needle fixing device for tumor clinical treatment provided by the present disclosure, two positioning supporting rods are fixedly mounted at a bottom of one side of the upright column, and the two positioning supporting rods are slidably connected to the moving seat. Ends of the two positioning supporting rods are fixedly connected to abutting disks.

According to the interventional needle fixing device for tumor clinical treatment provided by the present disclosure, by arranging the interventional needle adjustment mechanism, when facing tumor lesions in different positions, doctors can make the needle tube assembly realize left or right roll adjustment in the horizontal direction through the roll adjustment assembly, thereby accurately aligning the target area. At the same time, the pitch adjustment assembly can control the needle tube assembly to pitch upward or downward in the vertical direction, thereby meeting the diversified requirements of interventional needle angles in various complex surgical scenes, greatly improving the flexibility and accuracy of interventional needle puncture, and comprehensively improving the safety of surgical operation.

According to the interventional needle fixing device for tumor clinical treatment provided by the present disclosure, by arranging the displacement regulation mechanism, the overall position of the interventional needle fixing device can be flexibly adjusted according to the doctor's operation requirements when the interventional needle is used, thereby accurately locating the puncture position of the interventional needle, facilitating the doctor to quickly adjust the position of the device according to the specific situation of the patient and the operation requirements, ensuring the puncture accuracy of the interventional needle, and further improving the operation efficiency.

According to the interventional needle fixing device for tumor clinical treatment provided by the present disclosure, by activating the rotating assembly, the needle tube assembly can be driven to move in a circular motion, which enables the interventional needle to be smoothly embedded into the skin by means of mechanical rotary motion when in use, thereby significantly reducing the resistance in the puncture process and the discomfort of the patient, not only improving the puncture accuracy and safety, but also optimizing the treatment experience of the patient.

According to the interventional needle fixing device for tumor clinical treatment provided by the present disclosure, by arranging the positioning mechanism, the interventional needle fixing device can be conveniently mounted on a bed plate. In actual operation, the electric push rod is activated, and the power output will drive the clamping plate to move, the clamping plate can be tightly attached to the clamping base, thereby being firmly clamped to the bed plate. Compared with the traditional mounting method, this design greatly reduces the operation difficulty of medical staff, which is more convenient and labor-saving. Moreover, the positioning mechanism can adapt to bed plates with different sizes, which not only improves the universality of the device, but also ensures that the mounting of the fixing device can be completed quickly in a variety of clinical environments, further improving the efficiency of interventional needle operation.

BRIEF DESCRIPTION OF THE DRAWINGS

To explain the present disclosure or the technical solutions in the related art more clearly, a brief description will be given below with reference to the accompanying drawings which are used in the description of the examples or the related art. Obviously, the drawings in the description below are some examples of the present disclosure, and other drawings can be obtained according to these drawings without creative work for those ordinary skilled in the art.

Figure 1:
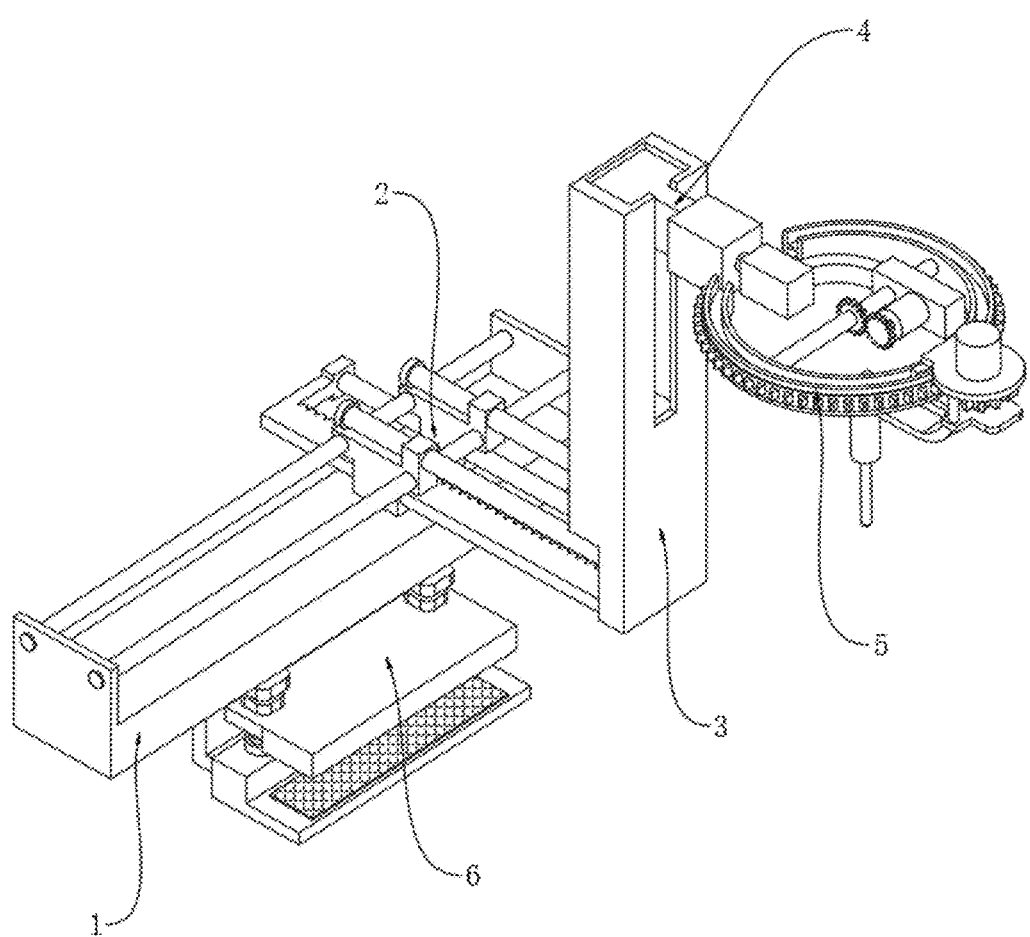
FIG. 1 is a schematic perspective view of an interventional needle fixing device for tumor clinical treatment according to an example of the present disclosure.

Reference numerals and denotations thereof:

1—supporting seat; 2—displacement regulation mechanism; 21—driving assembly; 211—driving motor; 212—lead screw; 213—fixing plate; 214—gear I; 22—moving assembly; 221—gear II; 222—moving seat; 223—gear rack; 224—sliding rod; 23—limiting rod; 3—upright column; 4—lifting mechanism; 41—electric telescopic rod; 42—lifting block; 43—mounting housing; 5—interventional needle adjustment mechanism; 51—roll adjustment assembly;

511—first motor; 512—supporting frame; 513—positioning rod; 514—annular frame; 52—pitch adjustment assembly; 521—second motor; 522—first gear; 523—second gear; 53—rotating assembly; 531—third motor; 532—third gear; 533—positioning frame plate; 534—sliding plate; 535—gear ring; 54—needle tube assembly; 541—mounting frame; 542—syringe; 543—needle guide tube; 6—positioning mechanism; 61—clamping base; 62—screw rod; 63—connecting rod; 64—electric push rod; 65—clamping plate; 7—positioning supporting rod; and 8—abutting disk.

DETAILED DESCRIPTION

To make the objects, technical solutions and advantages of the present disclosure more clear, technical solutions of the present disclosure will be described clearly and completely in the following with reference to the drawings of the present disclosure. Obviously, all the described examples are only some, rather than all examples of the present disclosure. Based on the examples in the present disclosure, all other examples obtained by those ordinary skilled in the art without creative efforts belong to the protection scope of the present disclosure.

Figure 2:
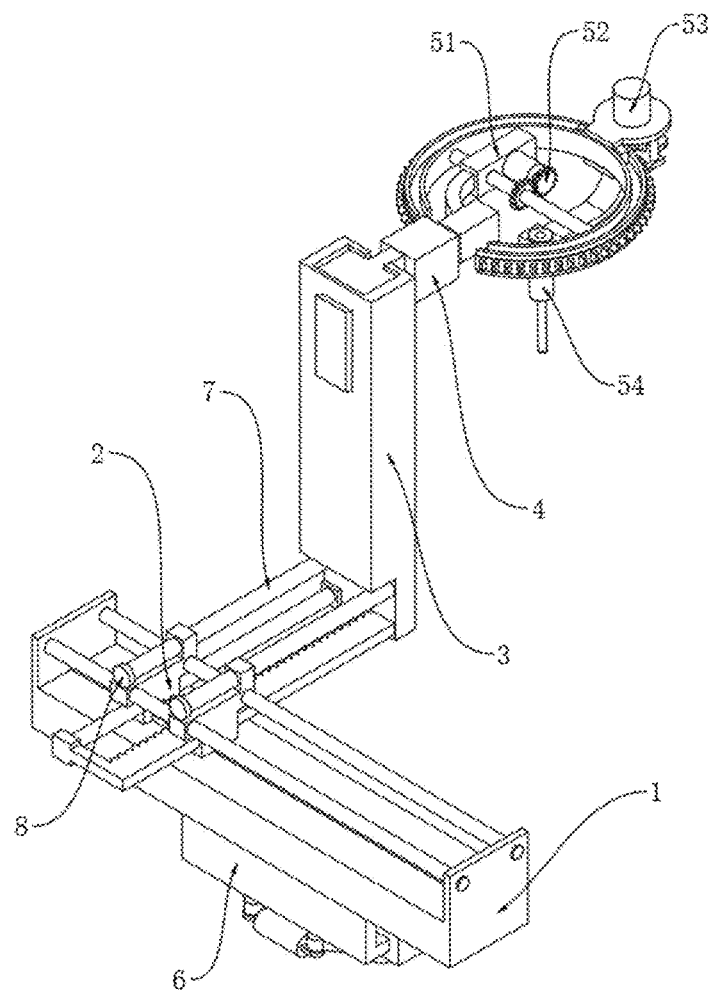
FIG. 2 is a schematic view of another perspective structure in FIG. 1.
Figure 3:
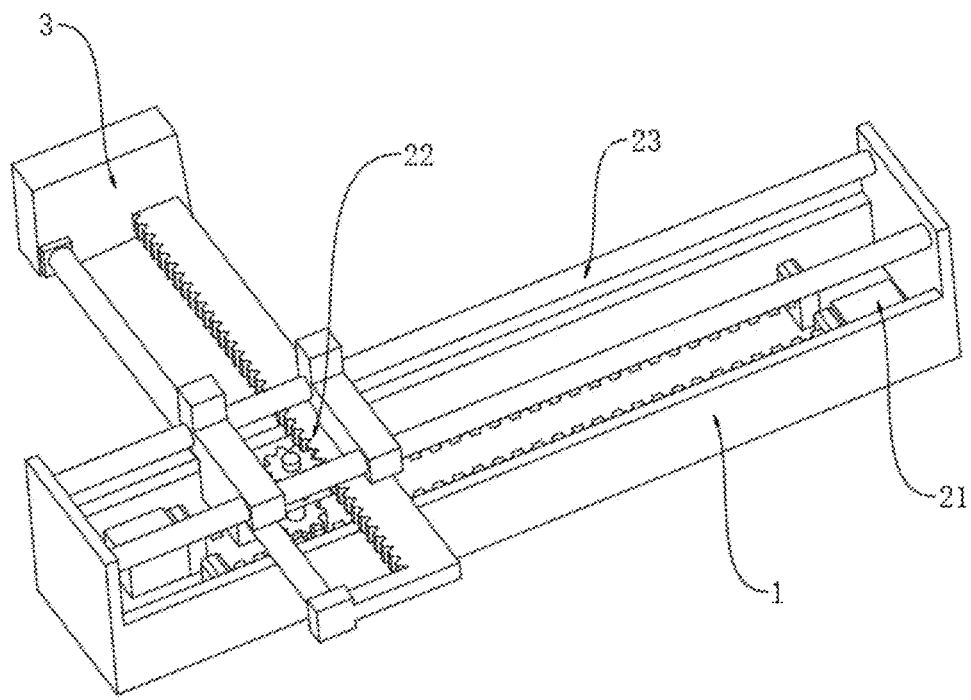
FIG. 3 is a schematic view of a local perspective structure in FIG. 2.
Figure 4:
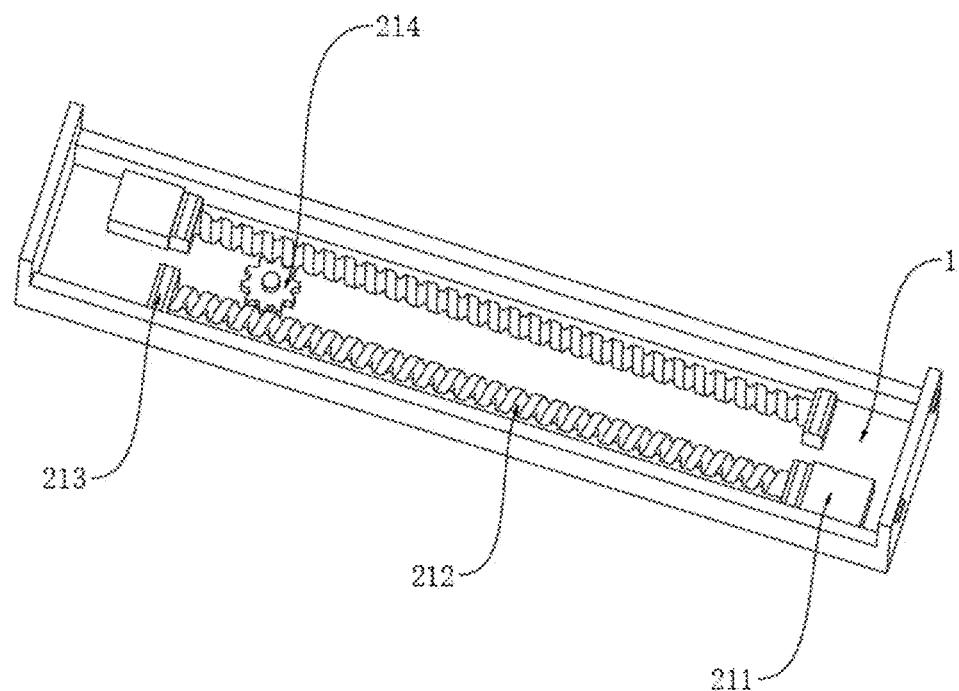
FIG. 4 is a schematic view of a local perspective structure in FIG. 3.
Figure 5:
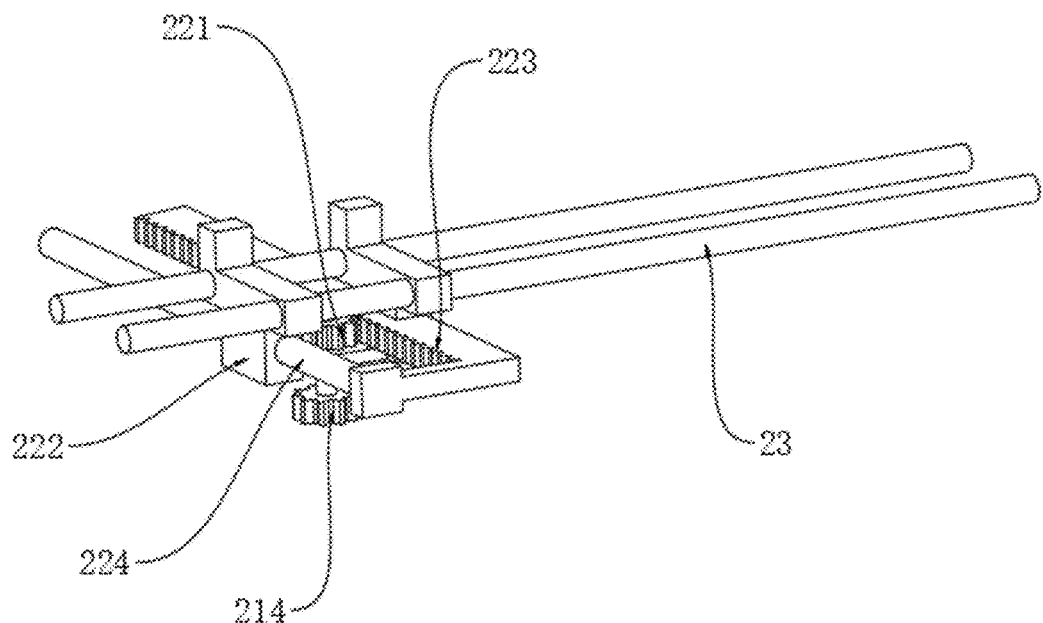
FIG. 5 is a schematic view of a partially disassembled perspective structure in FIG. 3.
Figure 6:
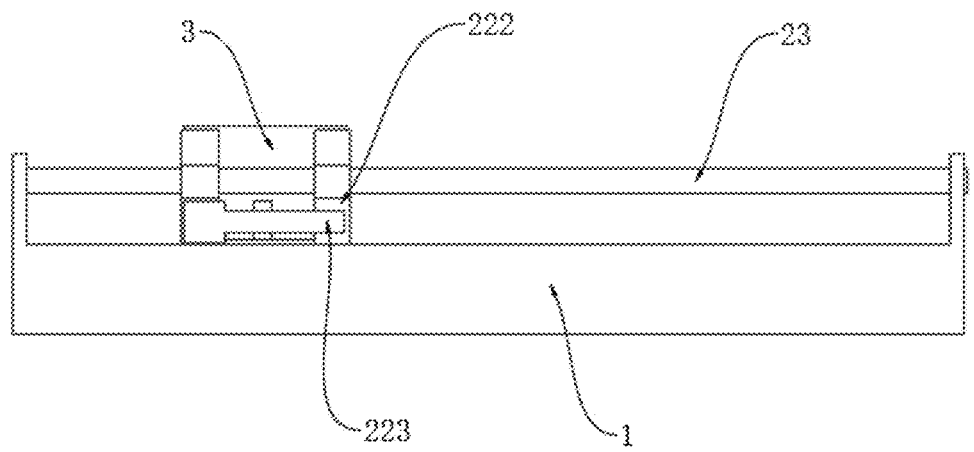
FIG. 6 is a side view of FIG. 3.

As shown in FIGS. 1-2, the present disclosure provides an interventional needle fixing device for tumor clinical treatment, which includes a supporting seat 1, a displacement regulation mechanism 2, an upright column 3, a lifting mechanism 4, an interventional needle adjustment mechanism 5, and a positioning mechanism 6.

The supporting seat 1 is a main structure of the whole fixing device, and is used for supporting and fixing other assemblies. The displacement regulation mechanism 2 is mounted in the supporting seat 1, an upper surface of the supporting seat 1 is disposed with a moving groove, and the displacement regulation mechanism 2 can be slidably adjusted in the moving groove. This design enables a main body driving part of the displacement regulation mechanism 2 to be hidden inside the supporting seat 1, thereby achieving effective protection and avoiding external interference and damage. The upright column 3 is fixed to the displacement regulation mechanism 2, and the position of the upright post 3 can be adjusted along with the movement of the displacement regulation mechanism 2. An accommodating cavity is arranged inside the upright column 3 for mounting the lifting mechanism 4. The lifting mechanism 4 can drive the interventional needle adjustment mechanism 5, and multi-angle adjustment can be realized by driving the interventional needle adjustment mechanism 5, thereby conveniently adjusting the inclination angle of the interventional needle to meet different operation requirements.

As shown in FIGS. 3-6, the displacement regulation mechanism 2 includes a driving assembly 21, a moving assembly 22, and two limiting rods 23. The driving assembly 21 is mounted in the supporting seat 1, and the moving assembly 22 is mounted on the driving assembly 21. The two limiting rods 23 are fixedly mounted on the supporting seat 1, and the limiting rods 23 are slidably connected to the moving assembly 22.

The driving assembly 21 is mounted in the supporting seat 1, and is used for driving the moving assembly 22 to realize the displacement adjustment in two directions. In an adjustment process, the moving assembly 22 can drive the interventional needle to move in front-rear and left-right directions, thereby accurately regulating the position of the interventional needle according to the use requirements of the interventional needle. In addition, two ends of the two limiting rods 23 are fixedly connected to two sides of inner walls of the supporting seat 1. The moving assembly 22 can slide on two limiting rods 23, and the function of the limiting rods 23 is to limit the movement trajectory of the moving assembly 22, ensure the moving assembly 22 to move smoothly in a predetermined direction, and prevent the moving assembly 22 from shifting or shaking in the adjustment process.

The driving assembly 21 includes two driving motors 211, two lead screws 212, two fixing plates 213, and a gear I 214. The two driving motors 211 are fixedly mounted on two sides of an inner cavity of the supporting seat 1. Ends of the two lead screws 212 are fixedly connected to output ends of the two driving motors 211, and the other ends are rotatably connected to the two fixing plates 213. The two fixing plates 213 are fixedly mounted in the supporting seat 1. The gear I 214 is meshed with the two lead screws 212.

The two lead screws 212 are positioned and mounted in two different rotation directions, and the two driving motors 211 are fixedly connected to opposite ends of the two lead screws 212. This design enables different operating states of the gear I to be generated when one of the driving motors 211 is activated. Specifically, when a certain driving motor 211 is activated, the driving motor 211 rotates the lead screw 212 connected to the driving motor 211. Since the two lead screws 212 are meshed with the gear I 214, the gear I 214 will rotate along with the rotation of the lead screws 212. Similarly, when the other driving motor 211 is activated, the driving motor 211 drives the other lead screw 212 to rotate to cause the gear I 214 to move along the rotational trajectory of the lead screw 212, thereby realizing the position adjustment of the gear I 214. In this way, the two driving motors 211 control the rotation direction and speed of the two lead screws 212, and realize the rotation and position movement adjustment of the gear I 214 to meet different operation requirements.

The moving assembly 22 includes a gear II 221, a moving seat 222, a gear rack 223, and a sliding rod 224. The gear II 221 is fixedly connected to the gear I 214. The moving seat 222 is movably connected to the two limiting rods 23. The gear rack 223 is slidably connected to the moving seat 222, and the gear rack 223 is meshed with the gear II 221. The sliding rod 224 is fixedly connected to the gear rack 223, and is movably embedded on a surface of the moving seat 222.

The gear I 214 is fixedly connected to the gear II 221 by a rotating rod, and the rotating rod is rotatably connected to the moving seat 222. Since the moving seat 222 is connected to the two limiting rods 23 by sliding, smooth support and limiting movement can be realized, ensuring the stability of the whole transmission system. One end of the gear rack 223 is fixedly connected to the sliding rod 224, and both of which are slidably connected to the moving seat 222. When the gear II 221 is meshed with the gear rack 223, the gear II 221 can drive the whole gear rack 223 to perform a movement operation. At this time, the sliding rod 224 moves on the moving seat 222 to play a limiting role, further enhancing the stability of the movement of the gear rack 223, and preventing the gear rack 223 from being shifted or swayed during the movement.

Figure 7:
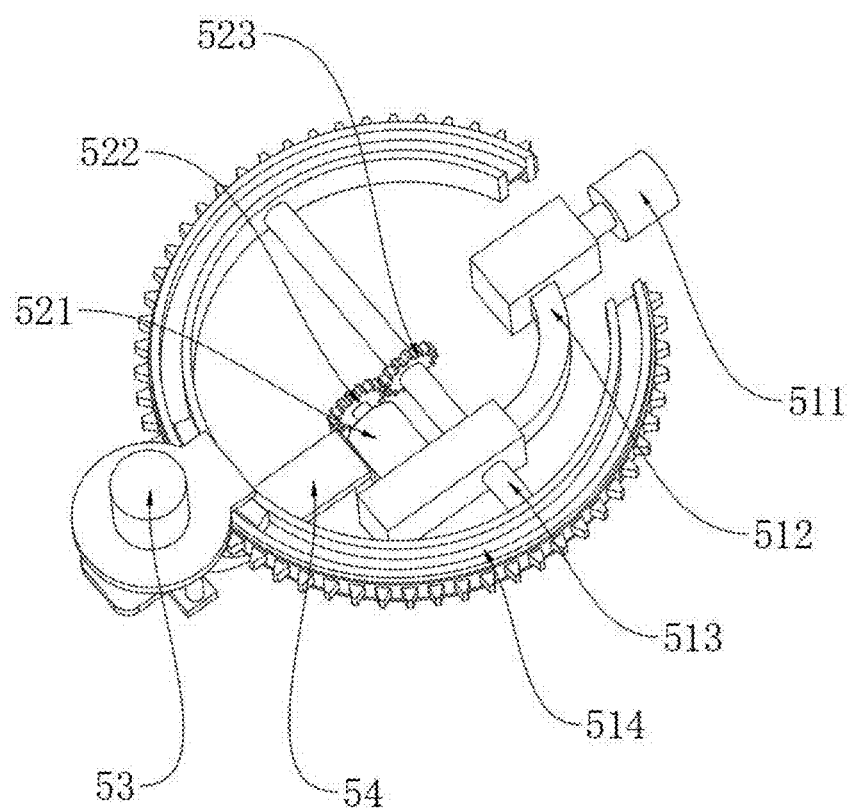
FIG. 7 is a schematic view of a perspective structure of an interventional needle adjustment mechanism in FIG. 1.
Figure 8:
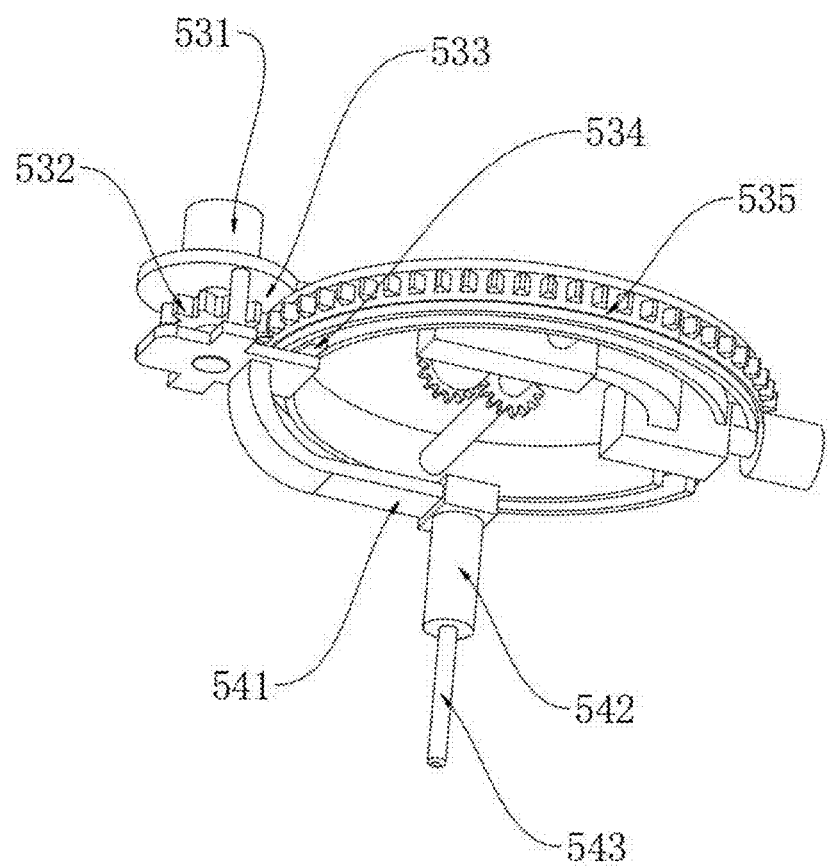
FIG. 8 is a schematic view of another perspective structure in FIG. 7.
Figure 9:
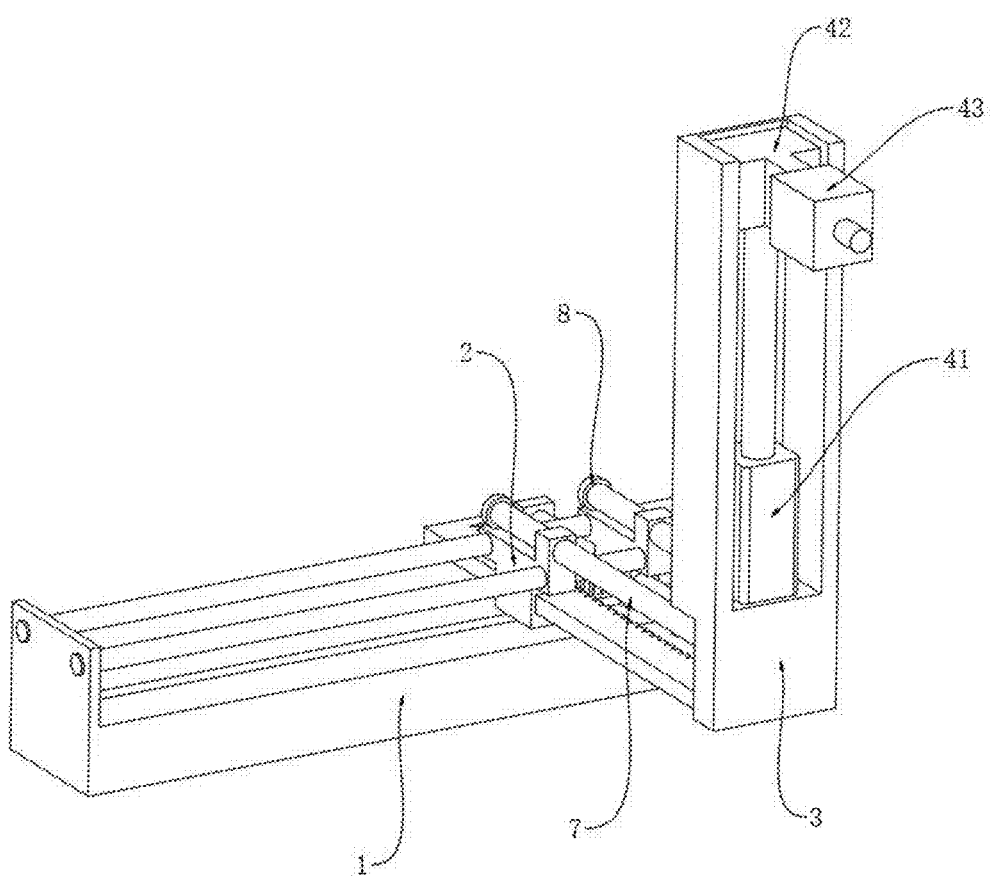
FIG. 9 is a schematic view of a local perspective structure in FIG. 1.

As shown in FIGS. 7-9, the interventional needle adjustment mechanism 5 includes a roll adjustment assembly 51, a pitch adjustment assembly 52, a rotating assembly 53, and a needle tube assembly 54. The roll adjustment assembly 51 is fixedly mounted in the lifting mechanism 4. The pitch adjustment assembly 52 is mounted on the roll adjustment assembly 51. The rotating assembly 53 is slidably connected to the roll adjustment assembly 51. The needle tube assembly 54 is mounted on the rotating assembly 53.

The roll adjustment assembly 51 is mounted in the lifting mechanism 4 by a supporting structure. When the roll adjustment assembly 51 is operated, left and right sides of the needle tube assembly 54 can be turned over and adjusted, thereby realizing the adjustment of left and right inclination angles of the needle tube assembly 54. This function is convenient for doctors to flexibly adjust the inclination angle of the interventional needle according to the specific conditions of the patient's skin surface in an interventional needle puncture process. When the pitch adjustment assembly 52 is operated, the needle tube assembly 54 can be driven to adjust the inclination of the upper and lower sides. Combined with the functions of the roll adjustment assembly 51 and the pitch adjustment assembly 52, the inclination angle adjustment of the needle tube assembly 54 in four directions can be realized to meet different operation requirements. When the rotating assembly 53 is operated, the needle tube assembly 54 is driven to move in a circular motion. This function enables the interventional needle to be smoothly embedded in the skin through mechanical movement when in use, reducing resistance and discomfort during puncture. The needle tube assembly 54 is used for loading the interventional needle, and realizes multifunctional adjustment under the cooperative action of the roll adjustment assembly 51, the pitch adjustment assembly 52, and the rotating assembly 53.

The roll adjustment assembly 51 includes a first motor 511, a supporting frame 512, a positioning rod 513, and an annular frame 514. The first motor 511 is fixedly mounted in the lifting mechanism 4, and the supporting frame 512 is fixedly connected to an output end of the first motor 511. The positioning rod 513 is movably embedded on the supporting frame 512. The annular frame 514 is fixedly connected to the positioning rod 513.

The first motor 511 is fixedly mounted in the lifting mechanism 4, and is supported by the lifting mechanism 4 to ensure that the first motor 511 can operate stably. When the first motor 511 operates, the supporting frame 512 as a whole is driven to rotate in the left-right direction, thereby realizing the roll adjustment of the related components. Two ends of the positioning rod 513 are fixed to the annular frame 514 to support and stabilize the annular frame 514. The annular frame 514 has an annular structure as a whole, and this design enables the annular frame 514 to cooperate with the surrounding structure to form an efficient adjustment mechanism. The positioning rod 513 passes through a surface of the supporting frame 512, and forms a movable connection with the supporting frame 512, which ensures the rotational freedom of the supporting frame 512. The stability of the overall structure is realized through the cooperation between the positioning rod 513 and the annular frame 514. Through this design, the rotational motion of the first motor 511 can realize the roll adjustment of the needle tube assembly 54 through the linkage of the supporting frame 512 and the annular frame 514, and meet the requirement of accurate control of the inclination angle in the interventional needle puncture process.

The pitch adjustment assembly 52 includes a second motor 521, a first gear 522, and a second gear 523. The second motor 521 is fixedly mounted on a surface of the supporting frame 512. The first gear 522 is fixedly connected to an output end of the second motor 521. The second gear 523 is fixedly mounted on the positioning rod 513, and the first gear 522 is meshed with the second gear 523.

The second motor 521 is fixedly mounted on the supporting frame 512. When the second motor 521 is activated, the first gear 522 will be driven to rotate. Since the second gear 523 is meshed with the first gear 522, the second gear 523 is also synchronously driven to rotate. In addition, the second gear 523 is fixedly connected to the positioning rod 513, which means that when the second motor 521 drives the first gear 522 to rotate, the second gear 523 and the connected positioning rod 513 will follow the rotation. Since the positioning rod 513 is connected to the annular frame 514, this rotational motion will also drive the body of the annular frame 514 to turn over.

The rotating assembly 53 includes a third motor 531, a third gear 532, a positioning frame plate 533, two sliding plates 534, and a gear ring 535. The third motor 531 is fixedly mounted on the positioning frame plate 533. One end of the third gear 532 is fixedly connected to an output end of the third motor 531, and the other end is rotatably connected to the positioning frame plate 533. The two sliding plates 534 are fixedly connected to two ends of the positioning frame plate 533. Two side surfaces of the annular frame 514 are disposed with sliding grooves movably connected to the two sliding plates 534. The gear ring 535 is fixedly sleeved on an outer surface of the annular frame 514, and the third gear 532 is meshed with the gear ring 535.

The third motor 531 is mounted on the positioning frame plate 533, upper and lower ends of the positioning frame plate 533 are clamped on the annular frame 514 through the two sliding plates 534, and upper and lower surfaces of the annular frame 514 are disposed with arc-shaped sliding grooves for sliding connection with the sliding plates 534. This design enables the sliding plates 534 to support the positioning frame plate 533 and to slide smoothly on the annular frame 514. When the third motor 531 is activated, the third gear 532 is driven to rotate, and the third gear 532 is meshed with the gear ring 535 fixed on an outer ring of the annular frame 514. In this meshing state, the rotation of the third gear 532 will move along a surface of the gear ring 535. Since the third motor 531 adopts a positive and reverse motor, the third gear 532 can move in two sides of the gear ring 535 by changing the rotation direction of the motor, thereby realizing the rotation motion of the positioning frame plate 533 and connecting components thereof.

The needle tube assembly 54 includes a mounting frame 541, a syringe 542, and a needle guide tube 543. The mounting frame 541 is fixedly connected to the positioning frame plate 533. The syringe 542 is fixedly mounted on a surface of the mounting frame 541. The needle guide tube 543 is embedded and mounted in the syringe 542.

The mounting frame 541 is fixedly mounted on a surface of the positioning frame plate 533 for supporting and mounting the syringe 542. An inside of the syringe 542 is disposed with a special groove for clamping the needle guide tube 543 to ensure that the needle guide tube 543 can be firmly mounted in the syringe 542, thereby maintaining stability during use. The needle tube assembly 54 is connected to the positioning frame plate 533 through the mounting frame 541, and can realize various angle adjustment under the cooperative action of the roll adjustment assembly 51, the pitch adjustment assembly 52 and the rotating assembly 53.

As shown in FIG. 9, the upright column 3 is fixedly mounted on one side of the moving assembly 22. The lifting mechanism 4 is arranged inside the upright column 3. The lifting mechanism 4 includes an electric telescopic rod 41, a lifting block 42, and a mounting housing 43. The electric telescopic rod 41 is fixedly mounted at a bottom of an inner cavity of the upright column 3. The lifting block 42 is fixedly mounted at a top of the electric telescopic rod 41. The mounting housing 43 is fixedly connected to the lifting block 42, and the first motor 511 is fixedly mounted inside the mounting housing 43.

One end of the upright column 3 is fixedly connected to the gear rack 223 and the sliding rod 224. The gear II 221 is driven to rotate when one of the driving motors 211 drives the lead screws 212 to rotate. Since the gear rack 223 is meshed with the gear 11221, the gear rack 223 moves between teeth of the gear II 221, thereby driving the upright column 3 as a whole to perform position adjustment. This design enables the upright column 3 to be accurately adjusted horizontally as required. An accommodating cavity is arranged inside the upright column 3 for mounting the lifting mechanism 4. When the electric telescopic rod 41 in the lifting mechanism 4 is activated, the height position of the lifting block 42 can be adjusted. In the movement of the lifting block 42, the lifting block 42 moves in the upright column 3 in a limited way, thereby ensuring the stability of the movement of the lifting block 42. Furthermore, the mounting housing 43 is fixed to the upright column 3 for supporting and mounting the first motor 511, thereby ensuring that the mounting housing 43 remains stable during operation.

Figure 10:
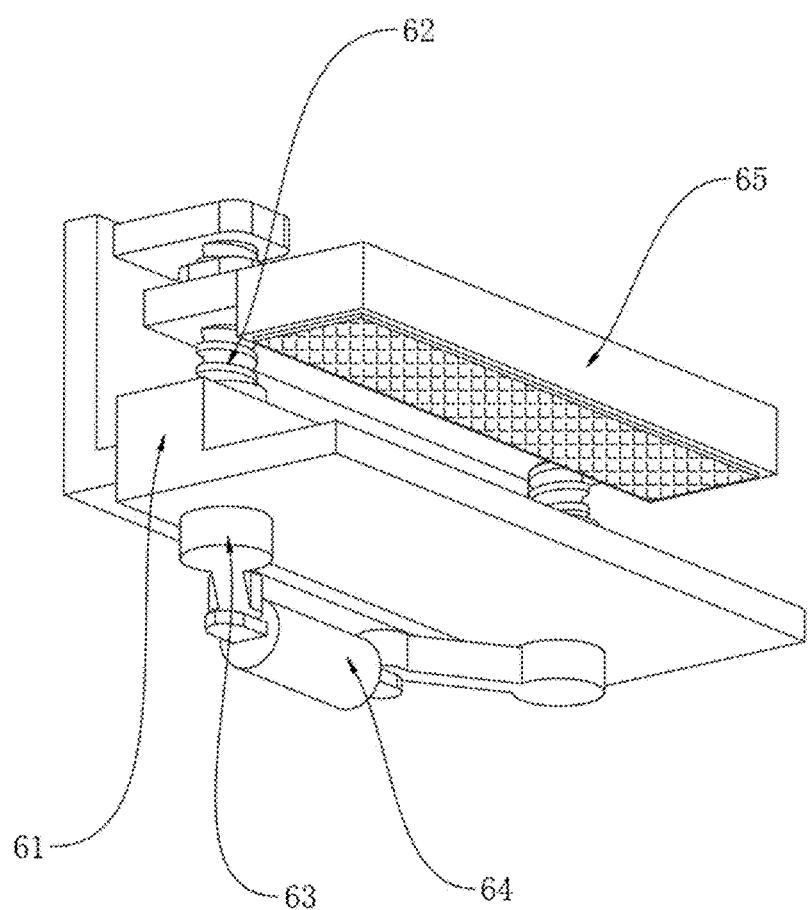
FIG. 10 is a schematic view of a perspective structure of a positioning mechanism in FIG. 1.

As shown in FIG. 10, the positioning mechanism 6 is fixedly mounted on a lower surface of the supporting seat 1. The positioning mechanism 6 includes a clamping base 61, two screw rods 62, two connecting rods 63, an electric push rod 64, and a clamping plate 65. The clamping base 61 is fixedly mounted on the supporting seat 1. Ends of the two screw rods 62 are movably connected to a lower surface of the clamping base 61, and the two screw rods 62 are fixedly connected to the two connecting rods 63. The electric push rod 64 is movably connected to the two connecting rods 63. The clamping plate 65 is screwed to the two screw rods 62. A lower surface of the clamping plate 65 and an upper surface of the clamping base 61 are arranged with anti-slip pads.

The clamping base 61 is integrally and fixedly mounted to a lower surface of the supporting seat 1. A clamping groove is formed between the clamping plate 65 and the clamping base 61, and the clamping groove can be used for clamping on the bed plate. In order to ensure the stability of clamping, the surfaces of the clamping base 61 and the clamping plate 65 in contact with the bed plate are arranged with anti-slip pads, sliding can be effectively prevented during clamping, and the stability of the device can be ensured. Two ends of the electric push rod 64 are movably connected to the two connecting rods 63. Ends of the two connecting rods 63 are movably embedded on the clamping base 61, and the two screw rods 62 are fixedly connected to the two connecting rods 63 by being embedded on the surface of the clamping base 61. Therefore, when the electric push rod 64 is activated, the two connecting rods 63 are driven to move, thereby causing the two screw rods 62 to rotate simultaneously. The clamping plate 65 is screwed to the two screw rods 62. When the two screw rods 62 rotate, the clamping plate 65 moves up and down along the axial direction of the screw rods 62. Since the rotation direction of the screw rods 62 and the moving direction of the clamping plate 65 are limited, this design can realize the accurate up-down movement of the clamping plate 65, thereby cooperating with the clamping base 61 to realize the clamping and fixing of the bed plate. When the whole fixing device is used, the clamping plate 65 and the clamping base 61 can be tightly clamped on the bed plate by the driving of the electric push rod 64, thereby ensuring that the device remains stable during surgery or operation without loosening or displacement.

Two positioning supporting rods 7 are fixedly mounted at a bottom of one side of the upright column 3, and the two positioning supporting rods 7 are slidably connected to the moving seat 222. Ends of the two positioning supporting rods 7 are fixedly connected to abutting disks 8. The two positioning supporting rods 7 are mounted on the upright column 3 through the support structure, and when the upright column 3 follows the displacement regulation mechanism 2 for movement adjustment, the positioning supporting rods 7 can move on the surface of the moving seat 222, thereby providing stable support for the upright column 3, ensuring that the upright column 3 is balanced and stable during movement, and avoiding shaking or offset caused by external force or vibration. In addition, the two abutting disks 8 are fixed to ends of the two positioning supporting rods 7, which can effectively prevent the positioning supporting rods 7 from being separated from the moving seat 222 during moving.

Working principles of the interventional needle fixing device of this example are as follows. Firstly, the positioning mechanism 6 is clamped on the bed plate, and the clamping groove formed between the lower surface of the clamping plate 65 and the upper surface of the clamping base 61 clamps the bed plate tightly. By driving the electric push rod 64, the operation of the electric push rod 64 will drive the two connecting rods 63 to generate offset, and the two screw rods 62 rotate synchronously. At this time, the clamping plate 65 located on the two screw rods 62 will move downward, and closely adhere to the bed plate with the clamping base 61 to achieve fixation. At this time, the whole fixing device has been positioned and mounted on the bed plate to prepare for the subsequent interventional needle treatment. When the position of the interventional needle needs to be adjusted, the two driving motors 211 can be activated. When one of the driving motors 211 is activated, the lead screws 212 rotate, thereby driving the gear I 214 to perform the movement operation, and the gear I 214 moves, driving the whole fixing device to perform the left and right position movement adjustment. When the other driving motor 211 is activated, the gear 1214 is driven to rotate by the lead screws 212, while the gear II 221 is driven to rotate, and the gear rack 223 is driven to move to realize the adjustment of the front and rear positions of the fixing device, thereby satisfying the adjustment and use of interventional needles at different positions. In the process of interventional needle treatment, firstly, the electric telescopic rod 41 is activated to drive the lifting block 42 to move downward, the needle guide tube 543 is lowered and punctured into the skin of the patient, and the use of the interventional needle is started. When the inclination angle of the interventional needle needs to be adjusted, the first motor 511 is activated, and the operation of the motor will drive the supporting frame 512 to rotate, thereby driving the annular frame 514 to turn over as a whole, causing the needle tube assembly 54 to follow the movement, realizing the adjustment of the left and right inclination angles, and satisfying the requirements of interventional needle puncture. When the second motor 521 is activated, the pitch inclination adjustment of the needle tube assembly 54 is realized through the meshing transmission of the first gear 522 and the second gear 523, and the insertion angle of the interventional needle is further optimized. In addition, when the interventional needle needs to be rotated, the third motor 531 is activated, and the third gear 532 rotates and moves on the surface of the gear ring 535, thereby driving the mounting frame 541 on the positioning frame plate 533 to rotate as a whole. Since the syringe 542 is mounted on a central position of the annular frame 514, this rotating motion can drive the main body of the needle guide tube 543 to rotate, and the interventional needle can smoothly enter the skin through rotation in the puncture process, thereby reducing the puncture resistance, and improving the use effect of the interventional needle and the comfort of the patient.

In this example, by arranging the displacement regulation mechanism 2, the position of the interventional needle fixing device can be adjusted, thereby meeting the use requirements in different scenarios. At the same time, by arranging the interventional needle adjustment mechanism 5, the doctor can adjust the inclination angle of the interventional needle according to the specific operation requirements in the interventional needle puncture, which not only improves the stability and accuracy of the operation, but also effectively reduces the error phenomenon caused by human factors. In addition, the synergistic effect of the displacement regulation mechanism 2 and the interventional needle adjustment mechanism 5 further optimizes the function of the whole fixing device, and the fixing device can better adapt to the complex clinical operation environment and provide all-round support for interventional therapy.

The device examples described above are merely schematic, in which the units described as separate components may or may not be physically separated, and the components displayed as units may or may not be physical units, that is, may be located in one place or may be distributed over multiple network units. Some or all of the modules may be selected according to actual needs to achieve the objective of the solution of this example. It can be understood and implemented by those skilled in the art without creative effort.

From the above description of the embodiments, those skilled in the art will clearly understand that each embodiment can be implemented by software and a necessary general hardware platform, and of course, it can also be implemented by hardware. Based on this understanding, the part of the above technical solution that essentially or contributes to the related art can be reflected in the form of a software product. This computer software product can be stored in computer-readable storage media, including read-only memory (ROM)/random access memory (RAM), floppy disks, optical discs, etc., including several instructions to enable a computer device to be a personal computer or a server, or a network device, or the like to perform the methods of various examples or certain portions of the examples.

Finally, it is to be noted that the above examples are merely used to illustrate the technical solutions of the present disclosure, and are not intended to limit the present disclosure. Although the present disclosure has been described in detail with reference to the foregoing examples, those skilled in the art will understand that the technical solutions disclosed in the above examples can still be modified, or some of the technical features thereof can be replaced by equivalents. However, these modifications and substitutions do not make the essence of the corresponding technical solutions depart from the spirit and scope of the technical solutions of various examples of the present disclosure.

The invention claimed is:

1. An interventional needle fixing device for tumor clinical treatment, comprising:
   a supporting seat (1);
   a displacement regulation mechanism (2), comprising a driving assembly (21), a moving assembly (22) and two limiting rods (23); the driving assembly (21) being mounted in the supporting seat (1), and the moving assembly (22) being mounted on the driving assembly (21); and the two limiting rods (23) being fixedly mounted on the supporting seat (1), and the limiting rods (23) being slidably connected to the moving assembly (22);
   an upright column (3), fixedly mounted on one side of the moving assembly (22);
   a lifting mechanism (4), arranged inside the upright column (3); and
   an interventional needle adjustment mechanism (5), comprising a roll adjustment assembly (51), a pitch adjustment assembly (52), a rotating assembly (53) and a needle tube assembly (54); and the roll adjustment assembly (51) being fixedly mounted in the lifting mechanism (4), the pitch adjustment assembly (52) being mounted on the roll adjustment assembly (51), the rotating assembly (53) being slidably connected to the roll adjustment assembly (51), and the needle tube assembly (54) being mounted on the rotating assembly (53).

2. The interventional needle fixing device for tumor clinical treatment according to claim 1, wherein the roll adjustment assembly (51) comprises a first motor (511), a supporting frame (512), a positioning rod (513), and an annular frame (514); and the first motor (511) is fixedly mounted in the lifting mechanism (4), the supporting frame (512) is fixedly connected to an output end of the first motor (511), the positioning rod (513) is movably embedded on the supporting frame (512), and the annular frame (514) is fixedly connected to the positioning rod (513).

3. The interventional needle fixing device for tumor clinical treatment according to claim 2, wherein the pitch adjustment assembly (52) comprises a second motor (521), a first gear (522), and a second gear (523); and the second motor (521) is fixedly mounted on a surface of the supporting frame (512), the first gear (522) is fixedly connected to an output end of the second motor (521), the second gear (523) is fixedly mounted on the positioning rod (513), and the first gear (522) is meshed with the second gear (523).

4. The interventional needle fixing device for tumor clinical treatment according to claim 3, wherein the rotating assembly (53) comprises a third motor (531), a third gear (532), a positioning frame plate (533), two sliding plates (534), and a gear ring (535); the third motor (531) is fixedly mounted on the positioning frame plate (533), one end of the third gear (532) is fixedly connected to an output end of the third motor (531), and the other end is rotatably connected to the positioning frame plate (533); and the two sliding plates (534) are fixedly connected to two ends of the positioning frame plate (533), two side surfaces of the annular frame (514) are disposed with sliding grooves movably connected to the two sliding plates (534), the gear ring (535) is fixedly sleeved on an outer surface of the annular frame (514), and the third gear (532) is meshed with the gear ring (535).

5. The interventional needle fixing device for tumor clinical treatment according to claim 4, wherein the needle tube assembly (54) comprises a mounting frame (541), a syringe (542), and a needle guide tube (543); and the mounting frame (541) is fixedly connected to the positioning frame plate (533), the syringe (542) is fixedly mounted on a surface of the mounting frame (541), and the needle guide tube (543) is embedded in the syringe (542).

6. The interventional needle fixing device for tumor clinical treatment according to claim 2, wherein the lifting mechanism (4) comprises an electric telescopic rod (41), a lifting block (42), and a mounting housing (43); the electric telescopic rod (41) is fixedly mounted at a bottom of an inner cavity of the upright column (3), the lifting block (42) is fixedly mounted at a top of the electric telescopic rod (41), the mounting housing (43) is fixedly connected to the lifting block (42), and the first motor (511) is fixedly mounted inside the mounting housing (43).

7. The interventional needle fixing device for tumor clinical treatment according to claim 1, wherein the driving assembly (21) comprises two driving motors (211), two lead screws (212), two fixing plates (213), and a gear I (214); the two driving motors (211) are fixedly mounted on two sides of an inner cavity of the supporting seat (1), ends of the two lead screws (212) are fixedly connected to output ends of the two driving motors (211), and the other ends are rotatably connected to the two fixing plates (213); and the two fixing plates (213) are fixedly mounted in the supporting seat (1), and the gear I (214) is meshed with the two lead screws (212).

8. The interventional needle fixing device for tumor clinical treatment according to claim 7, wherein the moving assembly (22) comprises a gear II (221), a moving seat (222), a gear rack (223), and a sliding rod (224); and the gear II (221) is fixedly connected to the gear I (214), the moving seat (222) is movably connected to the two limiting rods (23), the gear rack (223) is slidably connected to the moving seat (222), the gear rack (223) is meshed with the gear II (221), and the sliding rod (224) is fixedly connected to the gear rack (223) and is movably embedded on a surface of the moving seat (222).

9. The interventional needle fixing device for tumor clinical treatment according to claim 8, wherein two positioning supporting rods (7) are fixedly mounted at a bottom of one side of the upright column (3), the two positioning supporting rods (7) are slidably connected to the moving seat (222), and ends of the two positioning supporting rods (7) are fixedly connected to abutting disks (8).

10. The interventional needle fixing device for tumor clinical treatment according to claim 1, further comprising a positioning mechanism (6), fixedly mounted on a lower surface of the supporting seat (1), wherein the positioning mechanism (6) comprises a clamping base (61), two screw rods (62), two connecting rods (63), an electric push rod (64) and a clamping plate (65); the clamping base (61) is fixedly mounted on the supporting seat (1), ends of the two screw rods (62) are movably connected to a lower surface of the clamping base (61), and the two screw rods (62) are fixedly connected to the two connecting rods (63); and the electric push rod (64) is movably connected to the two connecting rods (63), the clamping plate (65) is screwed with the two screw rods (62), and a lower surface of the clamping plate (65) and an upper surface of the clamping base (61) are arranged with anti-slip pads.

\* \* \* \* \*